United States Patent [19]

Recktenwald

[11] Patent Number: 4,876,190

[45] Date of Patent: Oct. 24, 1989

[54] PERIDININ-CHLOROPHYLL COMPLEX AS FLUORESCENT LABEL

[75] Inventor: Diether J. Recktenwald, Cupertino, Calif.

[73] Assignee: Becton Dickinson & Company, Franklin Lakes, N.J.

[21] Appl. No.: 111,209

[22] Filed: Oct. 21, 1987

[51] Int. Cl.$^4$ .................. G01N 21/77; G01N 33/533

[52] U.S. Cl. ........................................... 435/7; 436/513; 436/537; 436/546; 436/800; 530/802

[58] Field of Search ............... 436/800, 537, 546, 513; 435/7; 530/802

[56] References Cited

U.S. PATENT DOCUMENTS 4,745,285  5/1988  Recktenwald .................. 356/318 X

OTHER PUBLICATIONS

Koka, P. et al., Biochimica et Biophysica Acta, 495, 220–231, (1977).
Chemical Abstracts, I, 99:35662p, (1983).
Chemical Abstracts, II, 101:148209z, (1984).

Primary Examiner—Robert J. Hill, Jr.
Attorney, Agent, or Firm—Richard L. Neeley

[57] ABSTRACT

Peridinin-chlorophyll-protein complexes are provided for use as fluorescent labels and are particularly useful in diagnostic assays employing as a reagent a fluorescent compound conjugated to a member of a specific binding pair, wherein the pair consists of a biochemical ligand and a receptor and the diagnostic assay comprises a step in which the conjugate binds to its complementary binding-pair member.

10 Claims, 3 Drawing Sheets

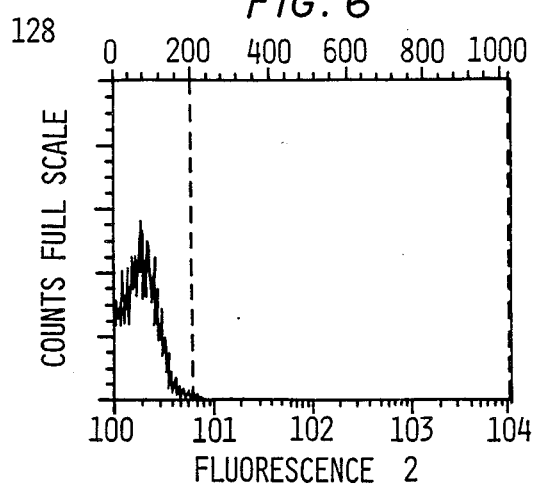
FIG. 6
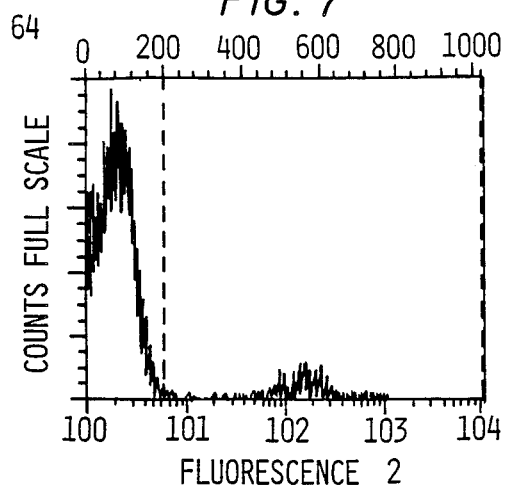
FIG. 7
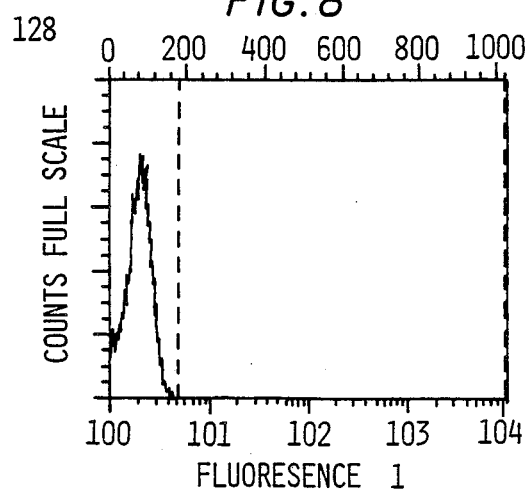
FIG. 8
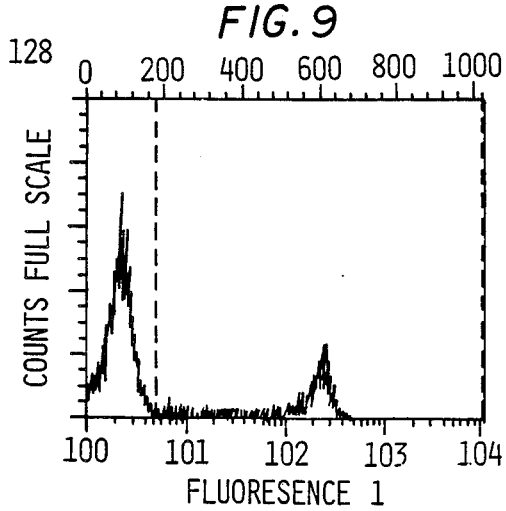
FIG. 9
FIG. 10
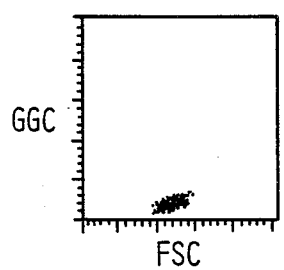
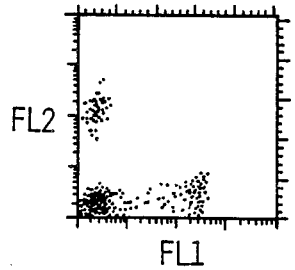
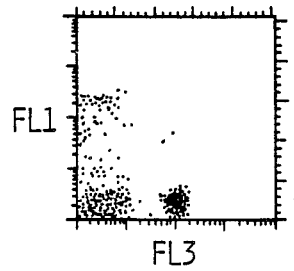
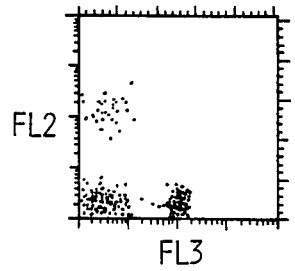

PERIDININ-CHLOROPHYLL COMPLEX AS FLUORESCENT LABEL

FIELD OF THE INVENTION

This invention relates to fluorophores used as labels on other molecules, typically for the purpose of detecting the presence of an interaction between the molecule to which the fluorophore is conjugated and another molecule, cell surface, or the like in a sample.

BACKGROUND OF THE INVENTION

The main types of fluorophores currently used as labels in diagnostic assays, such as immunoassays, are fluorecein, rhodamine, umbelliferone, and lanthanide chelates. Fluorescein is the most commonly used fluorophore since it is readily available in an activated form for direct coupling to antigens or antibodies. Both fluorescein and rhodamines show good chemical stability and have a proven record in actual use as labels. However, both fluorescein and the rhodamines have relatively small Stokes shifts, which limits the methodology that can be used in some respects. Both umbelliferones and lanthanide chelates have larger Stokes shifts, but their use as labels in immunoassays is relatively recent, and they are still untried in many respects. For example, the coupling between lanthanide chelates and antigens has presented some problems, and the fluorophore itself can be labile, which seriously restricts its use. Only a few assays have been published in which lanthanide chelates have been used as labels.

The problems seen with lanthanide chelates are indicative of the many constraints on the choice of fluorophore used in fluorescent labeling techniques. One constraint is the absorption and emission characteristic of the fluorophore, since many ligands, receptors, and materials associated with such compounds in the sample to be tested, e.g., blood, urine, or cerebrospinal fluid, will fluoresce and interfere with an accurate determination of the fluorescence of the fluorescent label. A second consideration is the quantum efficiency of the fluorophore, which should be high for good sensitivity. Another consideration is the ability to conjugate the fluorophore to ligands and receptors and the effect of such conjugation on the fluorophore. In many situations, conjugation to another molecule may result in a substantial change in the fluorescent characteristics of the fluorophore and, in some cases, substantially destroy or reduce the quantum efficiency of the fluorophore. Also of concern is whether the fluorescent molecules will interact with each other when in close proximity, resulting in self-quenching. An additional concern is whether there is non-specific binding of the fluorophore to other compounds or container walls, either by themselves or in conjunction with the compound to which the fluorophore is conjugated.

A recent development in the field of fluorescent labeling has been the use of phycobiliprotein conjugates Phycobiliproteins are a class of highly fluorescent proteins that form a part of the light-harvesting system in the photosynthetic apparatus of bluegreen bacteria and of two groups of eukaryotic algae, red algae and the cryptomonads. A particularly useful variation of their use comprises preparation of a phycobiliprotein tandem conjugate with a large Stokes shift. An example of such a conjugate is the covalent attachment of phycoerythrin to allophycocyanin. The resulting tandem conjugate has a large Stokes shift with an emission maximum at 660 nm and an excitation waveband that starts at about 440 nm. However, production of such tandem complexes requires the formation of a covalent or other chemical bond between the two components, therefore increasing the complexity of the production of the final conjugate.

Accordingly, there remains a need for fluorescent labels in diagnostic assays that have a large Stokes shift but which enjoy both stability and ease of preparation. Numerous techniques, such as histology, cytology, and immunoassays would enjoy substantial benefits from the availability of such a reagent.

RELEVANT LITERATURE

Peridinin-chlorophyll a-proteins, their properties, and methods of isolation are described in a number of publications including Haxo et al., *Plant Physiol.* (1976) 57:297-303: Song et al., *Biochemistry* (1976) 15:4422-4427; Prezelin and Haxo, *Planta (Berl.)* (1976) 128:133-144; and Koka and Song, *Biochim. Bio-phys. Acta.* (1977) 495:220-231. Proteinaceous fluorophores of the phycobiliprotein class are described in U.S. Pat. Nos. 4,520,110 and 4,542,104 and the publications cited therein.

SUMMARY OF THE INVENTION

Peridinin-chlorophyll-protein complexes are employed as fluorescent labels in systems involving binding reactions between members of a specific binding pair, such as immunoassays. The protein complexes are readily conjugated to other molecules and provide a large Stokes shift. The conjugated complexes have sufficient sensitivity and stability for use as fluorophores in diagnostic assays. The peridinin-chloro-phyll-protein complexes can be used individually, in combination with other proteinaceous fluorophores, or in combination with non-proteinaceous fluorophores.

BRIEF DESCRIPTION OF THE DRAWINGS

The invention will be better understood by reference to the following detailed description of specific embodiments when considered in combination with the drawings that form part of this specification, wherein:

FIG. 6 is a histogram of unstained cells for comparison with FIG. 7.

FIG. 7 is a histogram of cells stained with Leu—12—R.PE.

FIG. 8 is a histogram of unstained cells for comparison with FIG. 9.

FIG. 9 is a histogram of cells stained with Leu—2a—FITC. dot plots

FIG. 10 is a series of dot plots of different fluorescent channels showing cross-channel spillover for fluorescein (F11), phycoerythrin (F12) and PerCP (F13).

DESCRIPTION OF SPECIFIC EMBODIMENTS

Figure 1:
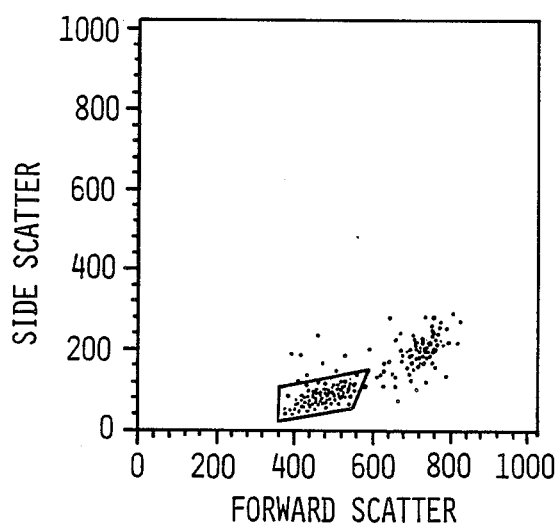
FIG. 1 is a histogram showing selection of lymphocytes used in a later-described example.

Compositions and methods are provided in Which peridinin-chlorophyll-protein complexes are conjugated to a member of a specific binding pair for use in any known or later discovered technique involving fluorescent labeling of analytes. The peridinin-chlorophyll-protein. complexes are readily available from natural sources or can be modified to provide novel complexes having different absorbance, emission, or labeling characteristics. These compositions find use for labeling of biochemical binding-pair members so that the resulting conjugates can be used in assays involving non-covalent binding to the complementary member of the specific binding pair. A wide variety of methods involve competitive or non-competitive binding of ligand to receptor for detection, analysis, or measurement of the presence of ligand or receptor.

Prior art teachings left doubt as to the ability of peridinin-chlorophyll-protein complexes to be used as labels in diagnostic assays. Diagnostic assays require a high degree of stability in order to avoid false positive or negative reactions resulting from changes in the fluorescent nature of the label. Koka et al., Biochim. Biophys. Acta. (1977) 495:220–231 indicates that photo-decomposition of chlorophyll a in PerCP complexes is avoided in the presence of oxygen because the peridinin present consumes the singlet oxygen that is produced. Consumption usually indicates reaction, which would also consume (i.e., destroy) the peridinin. If the amount of peridinin in a complex is continually being changed in a diagnostic system, as opposed to an in vivo system where repair is possible, the resulting decrease in absorbance would be contraindicative of the use of the PerCP complex in a diagnostic assay. Additionally, free PerCP is known to exhibit a significant amount of non-specific binding to biological components. It could no be determined whether this non-specific binding would adversely interfere with the use of PerCP to label specific binding compounds.

The conjugates of the subject invention are peridinin-chlorophyll-protein (PerCP) complexes bound either covalently or non-covalently, normally covalently, to a particular ligand or receptor. The proteinaceous portions of the PerCP complexes, referred to here as the apophotoproteins, have molecular weights of about 25,000 to 38,000 Daltons, typically about 32,000 Daltons. A number of apophotoproteins have been isolated from different biological sources and have pI values ranging from about 6.4 to 7.6. In some cases the apophotoprotein appears to be present as a dimer of identical or similar subunits having a molecular weight of from 15,000 to 16,000. Other apophotoproteins do not dissociate under the same conditions. Amino acid compositions for the apophotoproteins have been examined. Many are alanine rich and exhibit similar amino acid compositions.

The protein moiety of the PerCP complex forms about 90% (sometimes less) of the total complex. The remainder of the complex can be accounted for by a non-covalently bound chromophore comprising peridinin and chlorophyll molecules, typicaly chlorophyll a. However, chlorophyll a can be replaced by other types of chlorophyll by exchange reactions. The most common arrangement appears to be a 4:1 molar ratio of peridinin to chlorophyll a, although a 9:2 molar ratio has been reported. The complex that apparently has 9 peridinin molecules and 2 chlorophyll-a molecules appears to contain two complexes of peridinin with chlorophyll a spaced apart from one another. The chromophores appear to be accommodated in a hydrophobic crevice and not exposed to solvent. The surface of the apophotoprotein is itself highly hydrophilic. The actual structure (4:1 complex or 9:2 complex) is immaterial to the practice of this invention since sufficient surface area is present on the protein portion of the overall complex to allow use of the complex as a fluorescent label whichever structure is present.

It is possible to increase intensity of the fluorescent reaction by using cross-linked PerCP complexes as labels instead of individual complexes. The cross-linked complexes can be prepared by any of the protein-linking techniques described herein.

From the variety of phytoplanktons that have been examined, it appears that PerCP proteins are a normal component of peridinin-containing dinoflagellates. Members of the family Dinophyceae known to contain peridinin and therefore likely to contain PerCP complexes include *Zooxanthellae ex* (Tridacna species), *Amphidinium carterae* (Plymouth 450), *Cachonina niei*, *Gonyaulax polyedra*, Glenodinium species, *Amphidinium rhynocephaleum*, and *Gymnodinium splendens*. At least one strain of *Amphidinium carterae* identified as PY-1 is a notable exception as it contains copious quantities of peridinin but no PerCP complexes. The apophotoprotein of the complex appears to be well conserved between species. All natural isolates obtained to date contain the same peridinin molecule and chlorophyll a.

The presence of the apophotoprotein in the complex provides a wide range of functional groups for conjugation to proteinaceous and non-proteinaceous molecules. Functional groups which are present include amino, thio and carboxy. In some instances, it may be desirable to introduce functional groups, particularly thio groups where the apophotoprotein is to be conjugated to another protein.

Depending upon the nature of the molecule (e.g., member of a specific binding pair) to be conjugated to the complex, the ratio of the two moieties will vary widely, where there may be a plurality of binding pair members to one apophotoprotein. For small molecules, that is, of molecular weight less than 2,000d (daltons), generally greater than 100d, more typically greater than 150d, there will generally be on the average at least one and not more than about 100, usually not more than about 60 conjugated to a PerCP complex. With larger molecules, that is at least about 2,000 molecular weight, more usually at least about 5,000 molecular weight, the ratio of PerCP complex to ligand or receptor may vary widely, since a plurality of apophotoproteins may be present in the conjugate or a plurality of the specific binding pair member may be present in the conjugate. In addition, in some instances, initial intermediates are formed by covalently conjugating a small ligand to a PerCP complex and then forming a specific binding pair complex with the complementary receptor, where the receptor then serves as a ligand or receptor in a subsequent complex or is itself covalently attached to a ligand or receptor intended for use in a subsequent complex.

Specific binding pairs are often referred to as ligands and receptors, the term ligand referring to the smaller member of the pair. Binding pairs are said to exhibit specific binding when they exhibit a binding affinity (avidity of at least $10^7$, preferably at least $10^8$, more preferably at least $10^9$ liters/mole. The ligand may be any compound of interest for which there is a complementary receptor. The term ligand is intended to specifically exclude all compounds that might naturally be associated with a PerCP complex, such as water or other natural "ligands" associated with the PerCP complex. For the most part, the ligands of interest will be compounds having physiological activity, either naturally occurring or synthetic. One group of compounds will have molecular weights in the range of about 125 to 2,000, more usually from about 125 to 1,000, and will include a wide variety of drugs, small polypeptides, vitamins, enzyme substrates, coenzymes, pesticides, hormones, lipids, etc. These compounds for the most part will have at least one heteroatom, normally chalcogen (oxygen or sulfur) or nitrogen and may be aliphalitic, alicyclic aromatic or heterocyclic or combinations thereof. Illustrative compounds include epinephrine, prostaglandins, thyroxine, estrogen, corticosterone, ecdysone, digitoxin, aspirin, penicillin, hydrochlorothiazide, quinidine, oxytocin, somatostatin, diphenylhydantoin, retinol, vitamin K, cobalamin, biotin and folate.

Compounds of greater molecular weight, generally being 5,000 or more molecular weight, include poly(amino acids) including both polypeptides and proteins, polysaccharides, nucleic acids, and combinations thereof, e.g., glycosaminoglycans, glycoproteins, and ribosomes. These compounds can be either ligands or receptors, depending on the other member of the binding pair. Illustrative compounds include albumins, globulins, hemoglobulin, surface proteins on cells (such as T- and B-cell antigens, e.g., Leu, Thy, and Ia), tumor specific antigens, a-fetoprotein, retinol binding protein, C-reactive protein, enzymes, toxins, such as cholera toxin, diphtheria toxin, botulinus toxin, snake venom toxins, tetrodotoxin, saxitoxin, lectins (such as concanavalin, wheat germ agglutinin, and soy bean agglutinin), immunoglobulins, complement factors, lymphokines, mucoproteins, polysialic acids, chitin, collagen, and keratin.

Depending upon the molecule being labeled, a wide variety of linking groups may be employed for conjugating the PerCP complex to the other molecule. For the most part, with small molecules (those under 2,000 molecular weight), the functional group of interest for linking will be a carbonyl, either an aldehyde (to provide for reductive amination) or a carboxyl (which in conjunction with carbodiimide or as an activated ester, e.g., N-hydroxy succinimide) which will form a covalent bond with the amino groups present in the PerCP complex apophotoprotein: a thio ether or disulfide, where the apophotoprotein can be modified with an activated olefin and a mercapto group added or activated mercapto groups joined, e.g., Ellman's reagent: isothiocyanate: diazonium: nitrene: or carbene. Where the apophotoproteins are conjugated with a protein (for use either as a ligand or receptor), various bifunctional reagents may be employed, such as dialdehydes, tetrazolium salts, diacids, or the like, or alternatively, one or both of he two proteins involved may be modified for conjugation to the other protein: for example, a mercapto group may be present or be introduced on one protein and an activated olefin, e.g., maleimide, introduced into the other protein. Illustrative reagents include glutaraldehyde, bis-diazobiphenyl, maleimidoacetic acid NHS ester, methyldithioacetic acid NHS ester, and 3-(2'-pyridylthio)-propionic acid NHS ester (NHS is N-hydroxysuccinimidyl: other esters may also be used, such as p-nitrophenyl). For non-covalent bonding, various polyvalent receptors can be employed or combinations of receptors and ligands, such as antibodies, biotin-avidin, F(ab')$_2$, naturally occurring receptors, and the like.

There is ample literature for conjugating a wide variety of compounds to proteins. See for example A. N. Glazer, *The Proteins*, Vol. IIA, 3rd Ed., N. Neurath and R. L.. Hill, eds., Academic Press, pp. 1-103 (1976): A. N. Glazer et al., "Chemical Modification of Proteins", *Laboratory Techniques in Biochemistry and Molecular Biology*, Vol. 4, PRT I, T. S. . Work and E. Work, eds., North-Holland Publishing Co. (1975): and K. Peters et al., *Ann. Rev. Biochem.* (1977) 46:423-51, the descriptions of which are incorporated herein by reference. Examples of commercially available cross-linking reagents are disclosed in the Pierce 1981-82 Handbook and General Catalog, pp. 161-166, Pierce Chemical Co., Rockford, Illinois.

Known linking procedures as described in the above publications may be employed. For example, the protein portion of the PerCP complex can be reacted with iminothiolane, thereby placing an accessible sulf. hydryl group thereon. The other component of the conjugate may be activated by reaction with succinimidylpyridylthiopropionate. Mixture of the two prepared components of the conjugate results in joining thereof through disulfide bonds. Alternatively, instead of employing succinimidylpyridylthiopropionate, the second protein can be reacted with m-maleimidobenzoyl N-hydroxysuccinimide ester, and the resulting conjugate combined with the sulfhydryl-modified protein to form a thioether.

As previously indicated, instead of having a covalent bond between the specific binding pair member of interest and the apophotoprotein, non-covalent bonds may be employed. For example, if one wishes to conjugate a PerCP complex to avidin, biotin may be covalently conjugated to the PerCP ™ complex protein through a carboxyl group, and the resulting biotinylated PerCP complex combined with avidin, whereby a protein-labeled avidin will result. Furthermore, avidin can itself be attached to a variety of ligands and receptors, and the resulting conjugate can be used with a biotinylated PerCP complex (as an intermediate) to prepare the desired ligand/receptor-PerCP complex product.

The subject fluorophore compounds may be conjugated as labels to a wide variety of molecules. These conjugates may be used in a wide variety of ways, enhancing known methodologies for the detection, diagnosis, measurement and study of antigens and receptors, either present as individual molecules, or in more complex organizations, such as viruses, cells, tissue, organelles, e.g., plastids, nuclei, etc.

One of the uses of the subject conjugates is in fluorescent staining of cells. The cells may then be observed under a microscope, the presence of the fluorophore being diagnostic of the presence of a specific determinant site or the cells may be used in a fluorescence activated cell sorter (FACS). These techniques are described by Herzenberg et al., "Cellular Immunology", 3rd Ed., Chapt. 22, Blackwell Scientific Publications, 1978 (fluorescence-activated cell sorting): and by Goldman, "Fluorescence Antibody Methods", Academic Press, New York, 1968 (fluorescence microscopy and fluorescence staining). One or more of the PerCP complexes may be used. Alternatively, the PerCP complexes can be used in conjunction with fluorophores other than PerCP complexes, for example fluorescein, dansyl, umbelliferone, benzoxadiazoles, pyrenes, rose bengal, and/or phycobiliproteins, where the emission maxima are separated by at least about 15 nm, preferably at least about 25 nm.

By using combinations of fluorophores, one can provide for the detection of subsets of aggregations, such as particular types of cells, strains of organisms, strains of viruses, the natural complexing or interaction of different proteins or antigens, etc. Combinations of particular interest are combinations of fluorescein, biliprbteins, and PerCP complexes capable of being activated with the same laser light source. That is, substances which have absorption maxima in the range of about 450 to 550 nm.

Another use of the subject conjugates is in diagnostic assays, such as immunoassays or competitive protein binding assays, where the fluorescence emission may be measured at much higher wavelengths. Here, the complex may be conjugated to either a ligand or a receptor, particularly an antibody. While for the most part, the antibodies will be IgG, other antibodies such as IgA, IgD, IgE and IgM may also find use, as well as fragments of the immunoglobulins.

In addition, various naturally occurring receptors may be employed, particularly receptors having high binding specificity, such as avidin. By biotinylating either the receptor, the donor-acceptive conjugate or both, one can link various molecules through avidin.

A wide variety of fluorescent assays are known. A few of these assays are illustrated in U.S. Pat. Nos. 3,998,943: 3,985,867: 3,996,345: 4,036,946: 4,067,959: 4,160,016: and 4,166,105, the relevant portions of which are incorporated herein by reference.

The subject conjugates have the favorable properties of the PerCP complexes, such as (1) high absorption coefficients in the longer-wavelength visible spectral regions: (2) high fluorescence quantum yields: (3) long term stability, including good storage stability: (4) high water solubility: (5) ease of coupling to other molecules: (6) low non-specific binding when conjugated: (7) spectrum is maintained if uncoupled, in contrast to tandem complexes, which shift when uncoupled: and (8) large Stokes shift, so that background fluorescence is substantially diminished and one can observe fluorescence at very long wavelengths with little background interference resulting from scattering, fluorescence of normally encountered materials in samples, and the like. There is the further advantage that it is easier to work in the red end of the spectrum, rather than in the ultraviolet region, because typical plastic materials do not absorb and emit in the yellow to red spectral region.

The invention now being generally described, the same will be better understood by reference to the following examples which are provided for purposes of illustration only and are not intended to be limiting of the invention unless so specified.

EXAMPLES

Isolation and Purification of PerCP

Dinoflagellates were obtained by filtering ocean water in a red-tide area through a plankton net and collecting the particulate material. Ten g of algae were disrupted by vortexing in the presence of 75-150 µdiameter glass beads. The supernatant was isolated by centrifugation. The bulk of the non-PerCP protein was precipitated by adding 18 g of $(NH_4)_2SO_4$ to 50 ml of the suspension. Precipitate was removed by centrifugation, the supernatant was dialyzed against Tris buffer to remove $(NH_4)_2SO_4$ and concentrated to 1.3 ml by AMICON filtration. Pure PerCP was obtained by gel filtration on a 2.6 cm diamete$\times$47 cm Sephadex G-100 column. Fractions with a $A_{478}/A_{280}$ ratio greater than 3 were pooled and used for a conjugation of PerCP to streptavidin.

Spectroscopic Measurement

Absorption spectra were obtained on a Beckman model 25 spectrophotometer (Beckman Instruments, Inc., Fullerton, CA). Fluorescence spectra were obtained on a Perkin-Elmer model MPF-2A fluorometer.

Gel Chromatography

Coupling reactions were followed by gel chromatography on a Pharmacia Superose 12 or 6 FPLC gel filtration column which separates molecules primarily according to their hydrodynamic radii. In preparative experiments, 200-250 µl of sample was applied and 500 µfractions were collected. The eluting-buffer was 0.01 M phosphate-0.15 M NaCl (pH 7.2) or 0.05 M Tris-0.15 M NaCl (pH 7.8) and the flow rate was 0.5 ml/min.

Fluorescence Staining of Lymphocytes

Human peripheral blood leukocytes were prepared using Ficoll Hypague gradients. Viability counts of the cells recovered were done by staining the cells with acridine orange and ethidium bromide and counting fluorescent cells with a fluorescence microscope using standard fluorescein optics. This dye combination stains live cells green and dead cells orange-red. Cell preparation were always >95% viable.

The anti-Leu antibodies used in this study were all monoclonally derived hybridoma antibodies (Becton Dickinson & Co. Monoclonal Center, Mt. View, CA). The green fluorescence signal came from directly fluoresceinated antibodies. The orange fluorescence signal came from antibodies directly labeled with phycoerythrin. The red fluorescence signal came from biotinylated antibodies counter-stained with PerCP-avidin. Fluorescent antibody staining was done in one or two steps. Directly fluoresceinated antibodies were incubated with $10^6$ cells in 50 µl of Hank's MEM or PBS (0.01 M phosphate-0.15 M NaCL, pH 7.2) containing 2% (v/v) calf serum and 0.1% (w/v) azide for 20 min on ice. The amount of antibody added had been previously determined to be optimal for staining this number of cells for three-color staining. Both the directly labeled FITC- and PE-antibodies and the biotinylated antibody were incubated with $10^6$ cells in 50 µl of medium for 20 min on ice. After washing the cells twice with PBS, the PerCP-avidin conjugate was added to the cells in 50 µl of medium. This mixture was incubated for an additional 20 min on ice before finally washing the cells two times in PBS. Cells were resuspended in 0.5 ml of PBS for fluorescence analyses using the fluorescence-activated cell sorter.

Fluorescence-activated Cell Analyses

A Becton Dickinson & Co. Fluorescence-activated Cell Analyzer (FACScan) was used for fluorescence analyses of single cells. Electronic compensation (Loken et al., *J. Histochem. Cytochem.* (1977) 25:899-907) corrected for fluorescein spillover into the PE channel and for PE spillover into the FITC channel and for PE spillover into the PerCP channel. These corrected signals will be referred to as green, orange and red fluorescence. The fluorescence data was displayed as dot plots. Each dot depicts a single cell. The computer program that acquired and displayed the FACScan data in this manner is the Consort 30 Research Software from Becton Dickinson. Furthermore, the quantum yield and emission spectrum of the PerCP-avidin conjugates are virtually the same as those of native PerCP.

Preparation of Fluorescent Conjugate: PerCP-Avidin

As an example of a fluorescent conjugate of the invention, a PerCP-avidin conjugate was prepared. Thiolated PerCP (PerCP-SH) was prepared by the addition of 2-iminothiolane to PerCP. Activated avidin (IgG-S-S-Pyr) containing 2-pyridyl disulfide groups was prepared by the addition of N-succinimidyl 3(2-pyridyldithio)-propionate (SPDP). The fluorescent conjugate (PerCP-S-S-avidin) was then formed by mixing PerCP-SH with IgG—S—S—Pyr. The product was analyzed by gel chromatography on Pharmacia FPLC Superose 12. This gel filtration column separates molecules primarily according to their hydrodynamic radii. The reaction product PerCP—S—S-avidin emerges from the column much sooner than either reactant because the conjugate is larger than either component.

Preparation of Fluorescent Conjugate: PerCP-IgG

A second example of the joining of a PerCP to another molecule is provided by the synthesis of a PerCP-IgG conjugate. IgG was activated by the addition of SPDP. Sulfhydryl groups on thiolated PerCP then reacted with disulfide groups of activated IgG molecules.

Use of PerCP-Avidin to Label Biotinylated Beads

Polystyrene beads with primary amino groups on the particle surface were biotinylated using biotinsuccinimide. The fluorescence of the complex-avidin conjugate was tested by treating $10^6$ of these beads with the avidin-conjugate in 100 μl of phosphate buffered saline (PBS) with 10 μl of a solution of the avidin-conjugate at about 0.1 mg/ml. Unbound complex was removed by washing the beads by centrifugation in PBS. The PerCP-complex fluorescence of the conjugate was detected with a FACScan instrument, commercially available from Becton Dickinson. Fluorescence intensity histograms of the fluorescence-3 channel of the instrument for treated (with avidin-PerCP complex) and untreated beads showed that the PerCP complex was suitable for use as a fluorescent label for FACS.

Three-color Immunofluorescence Staining Experiment with PerCP—Leu—3

Human mononuclear peripheral blood cells were prepared as described in the application sheet "Preparation of Single Cell Suspension from Human Peripheral Blood", provided with the Becton Dickinson FACScan flow cytometer. Monocyte depletion was omitted. The cell suspension was adjusted to a concentration of $2 \times 10^7$ cells/ml. Fifty μl of this suspension were added to titered amounts of Leu—3a—PerCP, Leu—12—PE (phycoerythrin), and Leu—2a—FITC (fluorescein isothiocyanate) mixed, and incubated for 20 min on ice. One ml of phosphate buffered saline (PBS) was added and the cells were washed by centrifugation of $800 \times g$ for 5 min. After removal of the supernatant, the cell pellet was resuspended in 1 ml of PBS and analyzed.

Alternatively, cells were stained with Leu—b 3a—biotin in place of Leu-3a-PerCP, washed, and then stained with avidin-PerCP to detect the reaction of cells with Leu-3a-biotin. Another sample of cells was stained with avidin-PerCP only to investigate the non-specific binding properties of the dye-avidin conjugate.

Figure 2:
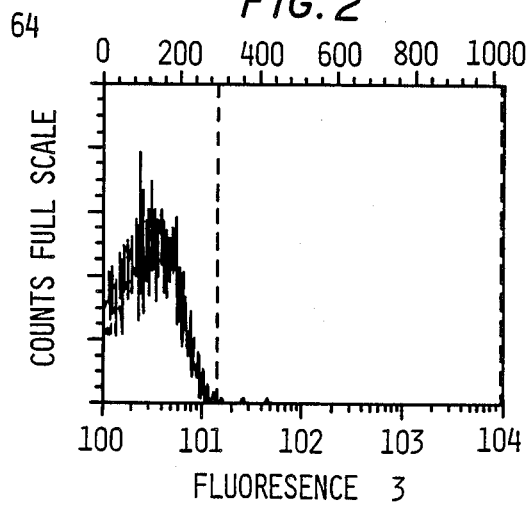
FIG. 2 is a histogram of unstained cells for comparison with FIG. 3.
Figure 3:
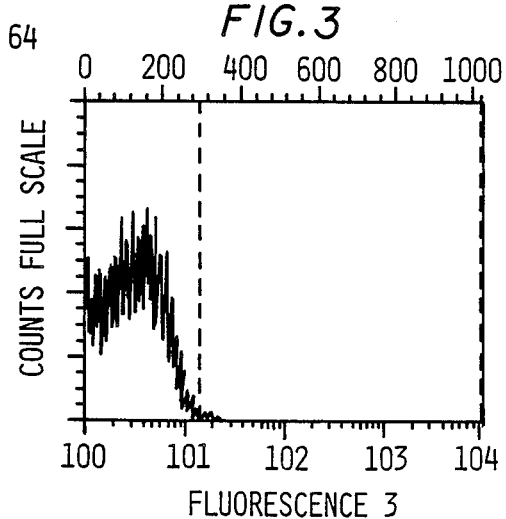
FIG. 3 is a histogram of cells stained with avidin—PerCP only.
Figure 4:
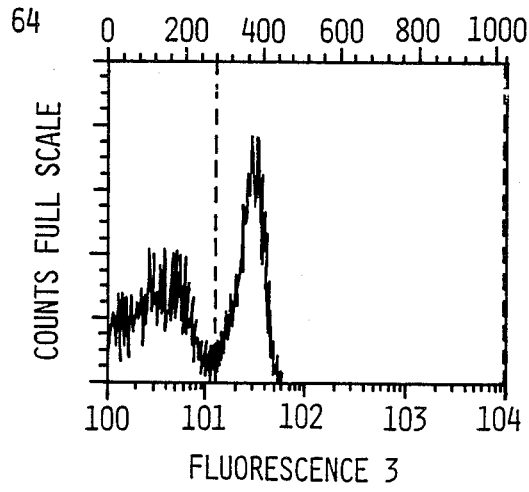
FIG. 4 is a histogram of cells stained with Leu—3a—PerCP.
Figure 5:
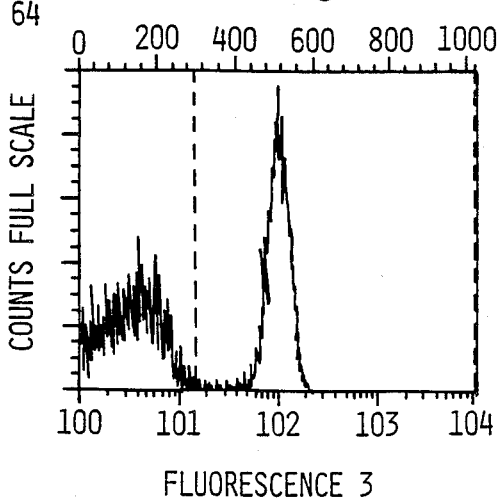
FIG. 5 is a histogram of cells stained with Leu—3a—biotin—avidin—PerCP.
Figure 11A:
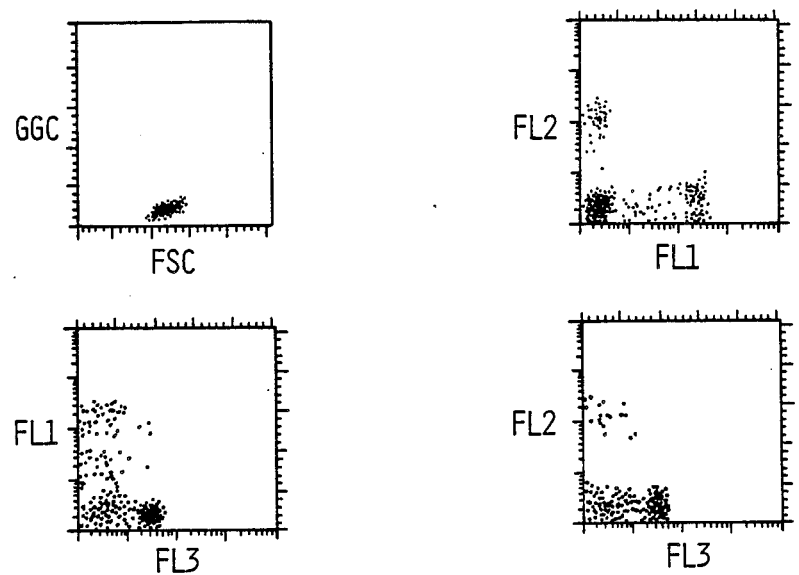
FIG. 11 is a series of four histograms from a three-color immunofluorescence assay using the labels of FIG. 10.
Figure 11B:
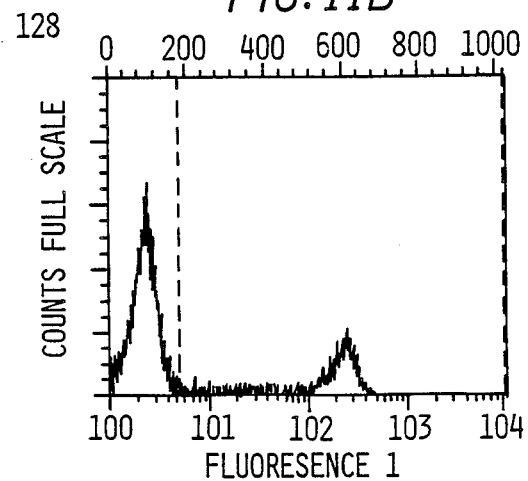
Figure 11C:
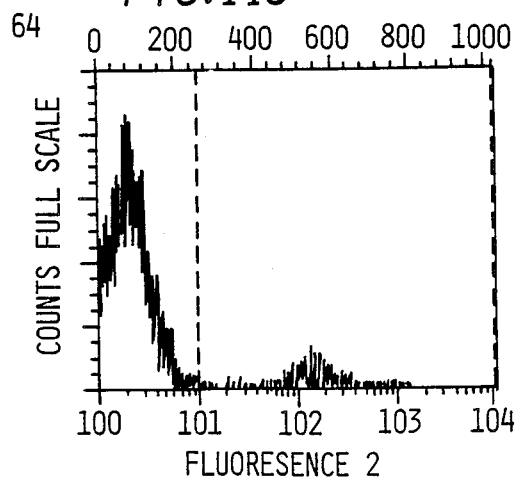
Figure 11D:
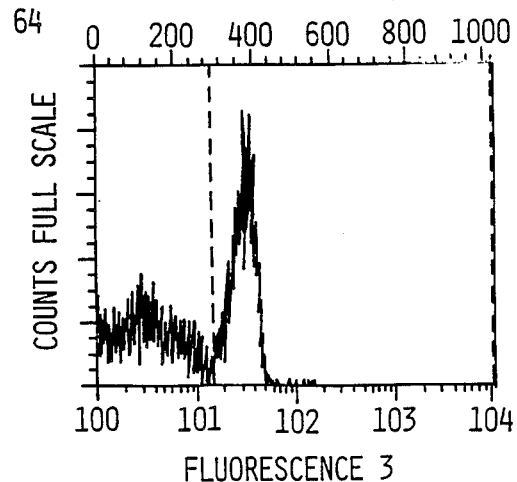

Analysis was carried out using a Becton Dickinson FACScan flow cytometer. This instrument measures forward scatter, side scatter, fluorescence emission at 530 nm (F11: FITC), at 575 nm (F12: PE) and above 640 nm (F13: PerCP). Data analysis was performed with a Consort 30 from Becton Dickinson. Lymphocytes were selected by gating-in the population with low forward scatter and low side scatter (FIG. 1). A comparison of a F13 histogram of unstained cells (FIG. 2) with one of cells stained with avidin-PerCP only (FIG. 3) shows negligible non-specific binding as evidenced by an only 2-channel shift. The unstained population of the Leu-3a-PerCP and the Leu-3a-biotin-avidin-PerCP staining experiments show a 13-channel shift (FIGS. 4 and 5) as compared to FIG. 2. For comparison a 6-channel shift was observed with Leu-12-R.PE (FIGS. 6 and 7), and an 11-channel shift with Leu-2a-FITC (FIGS. 8 and 9). These data show that non-specific staining by PerCP-labeled antibodies is negligible, comparable to that seen for FITC- and R.PE-labeled antibodies. The specific binding, as shown in the right portions of these Figures, is easily distinguishable from non-specific binding.

An advantage of PerCP conjugates over phycoerythrin conjugates is obvious from an examination of the settings of the multicolor compensation network of fluorescence spectra. In the experiment shown in FIG. 10, there is a 63% spillover of fluorescein fluorescence into the channel which detects PE fluorescence, and a 0.1% spillover of PE fluorescence into the fluorescein channel. There is 48% PE fluorescence in the PerCP channel, and no PerCP fluorescence in the PE channel. Spectral overlap from fluorescence emission spectra in Table 1 shows that there is no PerCP fluorescent in the fluorescein channel and less than 1% fluorescein fluorescence in the PerCP channel

TABLE 1

|  | FITC | PE | PerCP | |
|---|---|---|---|---|
|  | 520-540 | 565-585 | 640-660 | 660-680 |
| FITC | 100 | 21 | 0.85 | 0.34 |
| PE | 1.5 | 100 | 8.4 | N.D. |
| PerCP | 0* | 0* | 5 | 100 |

This demonstrates that the fluorescent dye pair fluorescein and PerCP can be used in an almost compensation-free two-color immunofluorescence system. Fluorescence-compensation has been a major trouble-spot in multicolor immunofluorescence analysis.

Three-color immunofluorescence using fluorescein, phycoerythrin, and PerCP is shown in FIG. 11. The fluorescein channel (F11) detects a-Leu-2a binding, identifying suppressor lymphocytes, the phycoerythrin channel detects α-Leu-12 (F12) binding, identifying B-cell lymphocytes, and the PerCP channel (F13) detects Leu-3a binding, identifying helper-cell lymphocytes. See panel A Histograms in panels B—D of FIG. 11, which compare the various channels, demonstrate a clear separation between stained and unstained cells (as shown by the marker), demonstrating the utility of this dye triplet for three-color immunofluorescence.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. In a diagnostic assay employing as a reagent a fluorescent compound conjugated to a member of a specific binding pair, wherein said pair comprises two biochemical molecules that bind specifically to each other and said diagnostic assay comprises a step in which the conjugated member of the specific binding pair binds to the other member of the specific binding pair, the improvement wherein
said flurescent compound is a peridinin-chloro-phyll-protein complex.

2. The diagnostic assay of claim 1, wherein the other member of said binding pair is a cell or cell surface antigen.

3. The diagnostic assay of claim 1, wherein said complex is a peridinin-chlorophyll a-protein complex.

4. The diagnostic assay of claim 1, wherein said complex is a peridinin-chlorophyll a-protein complex and said conjugated member of the specific binding pair is an immunoglobulin.

5. A fluorescent compound comprising a peridinin-chlorophyll-protein complex conjugated to a member of a specific binding pair, wherein said pair comprises two biochemical molecules that bind specifically to each other.

6. The compound of claim 5, wherein said conjugated member of said specific binding pair is a protein.

7. The compound of claim 6, wherein said conjugated member of said specific binding pair is such that it binds to a cell surface receptor or antigen.

8. The compound of claim 7, wherein said conjugated memer of said specific binding pair is an antibody and said specific binding pair is said antibody and an antigen to which said antibody specifically binds.

9. The compound of claim 5, wherein said complex is a peridinin-chlorophyll a-protein complex.

10. The compound of claim 5, wherein said conjugated member of said specific binding pair is an antigen and said specific binding pair is said antigen and an antibody specific for said antigen.

* * * * *